United States Patent [19]

Tanaka et al.

[11] Patent Number: 5,747,451
[45] Date of Patent: May 5, 1998

[54] PEPTIDE DERIVATIVES HAVING BINDING ACTIVITY TO MODIFIED LOW DENSITY LIPOPROTEIN

[75] Inventors: Toshiki Tanaka, Osaka; Takefumi Doi, Ibaraki; Haruki Nakamura, Toyonaka; Takeshi Imanishi, Nara; Tatsuhiko Kodama, Tokyo, all of Japan

[73] Assignee: Protein Engineering Research Institute, Osaka, Japan

[21] Appl. No.: 395,816

[22] Filed: Feb. 28, 1995

[30] Foreign Application Priority Data

Nov. 22, 1994 [JP] Japan ..................... 6-288465

[51] Int. Cl.$^6$ .................. A61K 38/16; A61K 38/10; C07K 14/00; C07K 7/00
[52] U.S. Cl. ................ 514/12; 514/13; 514/14; 530/324; 530/326; 530/327
[58] Field of Search ................... 530/324, 326, 530/327; 514/12, 13, 14, 21

[56] References Cited

PUBLICATIONS

Fields, "Mini–Collagens" (1993) Caplus # 1995:69258.
Fields, "Synthesis Collagen Sequences" (1993) Biosis # 94:12188.

C. Fields et al., "Solid–Phase Synthesis and Stability of Triple–Helical Peptides Incorporating Native Collagen Sequences", Biopolymers, vol. 33, Issue 10, pp. 1695–1707, Oct. 1993.

T. Tanaka et al., "A Synthetic Model of Collagen Structure taken from Bovine Macrophage Scavenger Receptor", FEBS 13257, vol. 334, No. 3, pp. 272–276, Nov. 1993.

*Primary Examiner*—Cecilia J. Tsang
*Assistant Examiner*—Patrick R. Delaney
*Attorney, Agent, or Firm*—Wenderoth, Lind & Ponack

[57] ABSTRACT

Peptide derivatives represented by the formula (I):

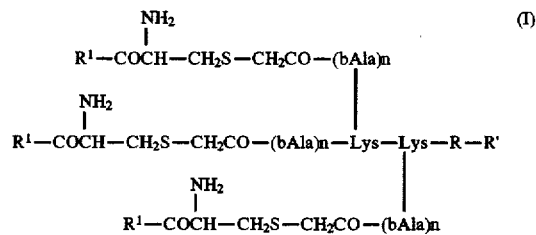

which can specifically bind to modified LDL in competition with scavenger receptors on macrophages and are useful in diagnosing, preventing and treating circulatory diseases caused by accumulation of modified LDL in macrophages.

10 Claims, 7 Drawing Sheets

SEQUENCE LISTING ( 1 ) GENERAL INFORMATION:

( i i i ) NUMBER OF SEQUENCES:2

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Gly  Lys  Thr  Gly  Lys  Pro  Gly  Leu  Asn  Gly  Gln  Lys  Gly
 1                 5                             10
Gln  Lys  Gly  Glu  Lys
                15
```

( 2 ) INFORMATION FOR SEQ ID NO:2:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear     ( i i ) MOLECULE TYPE: peptide

( i x ) FEATURE:
        ( A ) NAME/KEY: modified site
        ( B ) LOCATION: 4, 7, 10, 13, 34, 37, 40
        ( C ) IDENTIFICATION METHOD:
        ( D ) OTHER INFORMATION: /note="4 Hyp"

( x i ) SEQUENCE DESCRIPTION: SEQ ID NO:2:

```
Cys  Gly  Pro  Xaa  Gly  Pro  Xaa  Gly  Pro  Xaa  Gly  Pro  Xaa
 1                 5                             10
Gly  Lys  Thr  Gly  Lys  Pro  Gly  Leu  Asn  Gly  Gln  Lys  Gly
                15                  20                   25
Gln  Lys  Gly  Glu  Lys  Gly  Pro  Xaa  Gly  Pro  Xaa  Gly  Pro
                30                             35
Xaa  Gly
 40
```

PEPTIDE DERIVATIVES HAVING BINDING ACTIVITY TO MODIFIED LOW DENSITY LIPOPROTEIN

BACKGROUND OF THE INVENTION

1. Field of the Invention

The present invention relates to novel peptide derivatives which can specifically bind to an acetylated low density lipoprotein (hereinafter referred to as "LDL").

2. Description of Related Art

Since a value indicating the cholesterol level in blood has a positive correlation with circulatory diseases (e.g. arterial sclerosis, etc), drugs for decreasing the cholesterol level have intensively been developed. Typical examples thereof include drugs for inhibiting in vivo synthesis of cholesterols (e.g. Compactin, Mevalotin, etc.) and drugs for inhibiting the absorption of cholesterol through enteric canal (e.g. Colestyramine, Cholestipol, etc.). Additionally, drugs (e.g. Probucol, etc.) which do not decrease a LDL level in blood but depress the oxidation of LDL thereby preventing arterial sclerosis have already been put in practical use.

On the other hand, a foamy macrophage is known to appear following the uptake of modified LDL such as oxidized or acetylated low density lipoprotein (AcLDL) and the like, which results in cholesterol deposition, in the initial lesions of arterial sclerosis. On the basis of this observation, the development of drugs capable of preventing cholesterols from accumulating in macrophages has been attempted. Although an inhibitor of acyl-CoA cholesterol acyltransferases has been suggested to be useful [Brown, M. S., Ann. Rev. Biochem., 52, 223–261, 1983] for such a purpose, no drugs capable of depressing/inhibiting the incorporation of modified LDL into macrophages have been provided so far.

The incorporation of modified LDL into macrophages is effected through the binding of modified LDL to scavenger receptors on the cell surface of macrophages, which is followed by the incorporation of modified LDL into cells by endocytosis. Accordingly, a compound which has an affinity for the modified LDL and can bind to the same in competition with its natural receptors can inhibit the binding between modified LDL and receptors on macrophages thereby depressing and/or delaying the onset of diseases associated with modified LDL in blood, particularly circulatory diseases (e.g. arterial sclerosis, cardiac infarction, angina pectoris, cerebral hemorrhage, etc.), relieving symptoms of patients. Such a compound, when immobilized on a suitable solid phase carrier and brought into contact with circulatory blood, can fix modified LDL onto the solid phase carrier. The immobilized-modified LDL is then removed from blood in order to clarify blood or diagnose diseases through the determination of a concentration of modified LDL in blood. Thus, the immobilized peptide would be useful for diagnosing, depressing or treating various diseases associated with modified LDL, e.g., arterial sclerosis, etc.

However, since the scavenger receptor is a membrane protein of a molecular weight of 70 KDa existing as a large molecule in the form of trimer (Kodama et al., Nature, 1990, 343, 531–535), it is difficult to synthesize a peptide corresponding to the receptor molecule itself.

It has been thought that the binding site of modified LDL on the scavenger receptor is present in a collagen-like domain comprising a repeating sequence of tripeptides, Gly-X-Y (X and Y are independently a variable amino acid), at its carboxy-terminus. Particularly, it has been suggested that the binding site is located within 22 residues at the carboxy-terminus of the collagen-like domain and that lysine at 327, 334, 337 and 340, in particular the one at 337 plays an important role (Doi et al., J. Biol. Chem., 1993, 268, 2126–2133).

Accordingly, the above object can be accomplished by synthesizing a peptide(s) having the same binding activity as that of the collagen-like domain of a scavenger receptor which part is responsible to the binding with modified LDL. The synthesis of such a peptide, however, has been hindered because a natural collagen-like domain of scavenger receptor takes complicated structure wherein the amino-termini of three peptides chain are interacted and the identification of a given structure of a peptide having a binding activity was very difficult.

SUMMARY OF THE INVENTION

The present inventors have now succeeded in identification of the site on the scavenger receptor molecule participating in the binding with a modified LDL and have synthesized peptide derivatives having a binding activity to modified LDL.

Thus, the present invention provides a compound of the formula (I):

wherein:

bAla is β-alanine;

$R^1$ is a group selected independently from peptide residues represented by the formula:

wherein 4Hyp is 4-hydroxyproline,

$R^2$ is a peptide residue having 9 to 72 amino acids, $R^3$ is an optionally modified glycine residue, and q is an integer selected independently from 0 to 10;

n is an integer of 0 to 4;

R is a peptide residue having 0 to 5 amino acids or a group represented by the formula:

wherein Acp is 6-aminocaproic acid; and

R' is a group selected from an optionally modified tyrosine residue, an optionally modified tryptophan residue and any compound residues usable in the quantitative determination of the peptide.

DETAILED DESCRIPTION OF THE INVENTION

The compounds (I) of the present invention advantageously contains 3 peptides represented by $R^1$ which, when bound together, provide a collagen-like structure analogous to that of the scavenger receptor. A peptide of this structure is known to be stabilized when several repeating units of a tripeptide represented by Gly-Pro-4Hyp (4Hyp indicates 4-hydroxyproline) are contained in the amino- and/or carboxy-terminal regions of said peptide moieties $R^1$ (Thakur. S. et al., Biopolymers, 1986, 25, 1081–1086).

Accordingly, it is preferred to insert repeating units of the tripeptide Gly-Pro-4Hyp at the amino- and carboxy-termini of the peptide residue $R^2$, which is thought to be the binding site of modified LDL and preferably contains at least 4 lysine residues. Thus, such a repeating unit can be inserted more than one time, preferably 2–8 times, more preferably 4 times at the amino-terminus, and more than one time, preferably 2 to 8 times, more preferably 3 times at the carboxy-terminus. Alternatively, an amino acid(s) other than lysine contained in amino acid sequence of $R^2$ can be replaced with other amino acid(s) to convert a partial sequence to Gly-Pro-R. Furthermore, it is possible to replace neutral and/or acidic amino acid(s) with lysine or other basic amino acid(s) (e.g. ornithine, etc.) so as to strengthen the bond with a ligand. It is also possible to prepare a compound having a cysteine or mercaptopropyl group at the amino-terminus of the peptide, which compound can bind to a compound represented by the formula (III):

(III)

wherein X is halogen, and R, R', bAla and n are as defined above.

All compounds of the formula (I) as defined above are preferred for purposes of the present invention. However, compounds (I) wherein n is 1 to 2, $R^2$ is a peptide residue which comprises 9 to 72 amino acids containing at least 4 lysine residues and q is 2 to 8 are preferred, and those wherein n is 2, q is 3 or 4 and $R^2$ is a peptide residue represented by the SEQ ID NO: 1 of the Sequence Listings are more preferred.

The term "an optionally modified glycine residue" in the definition of $R^3$ means that a carboxyl group of the glycine residue may be in a free state, or amidated or esterified. Examples of the ester include methyl, ethyl, butyl, benzyl ester and the like.

The term "a group selected from an optionally modified tyrosine residue, an optionally modified tryptophan residue and any compounds usable in the quantitative determination of the peptide" in the definition of R' means that a carboxyl group of the amino acid residue may be in a free state, or amidated or esterified, similar to the above definition. Examples of the ester include methyl, ethyl, butyl, benzyl ester and the like.

The presence of the amino acid residues or their derivatives or the compounds cited above in peptides as R' facilitates the quantitative determination of said peptides. For example, if the tyrosine or tryptophan residue is present, the quantitative determination of peptides can be easily conducted by measuring the absorption at 280 nm.

The term "halogen" means chloro, bromo and iodo, and bromo is preferred.

It has been demonstrated that the peptide derivative (I) of the present invention specifically binds to AcLDL and is, therefor, considered to be a receptor of modified LDL, as is described in detail in Examples below.

Accordingly, the compound (I) of the present invention can be administered to persons who are liable to suffer from various diseases associated with modified LDL (e.g. arterial sclerosis, etc.) or patients who have already been suffered from these diseases to prevent or treat such diseases through the inhibition or depression of uptake of modified LDL by macrophages.

The compound of the formula (I) having a biotin moiety can be optionally immobilized onto a solid phase carrier through the biotin moiety to give an immobilized peptide. The resulting immobilized peptide can be useful in the prevention or treatment of diseases by bringing it into contact with circulating blood to remove modified LDL in blood. It can be also used to determine the concentration of modified LDL in blood thereby contributing to the diagnosis, treatment or prophylaxis of diseases. The immobilized peptide can be advantageously provided in the form of a kit for the purpose of diagnosing and treating.

Accordingly, the present invention also provides a pharmaceutical composition containing the compounds (I) for inhibiting the incorporation of modified LDL in blood by macrophages. The pharmaceutical composition can be useful for preventing or treating various diseases associated with modified LDL, e.g. arterial sclerosis, etc.

Further, the present invention also provides an immobilized peptide having a binding activity to a modified LDL, wherein the compounds (I) are immobilized on a suitable solid phase carrier.

The peptide compounds (I) of the present invention can be immobilized on solid phase carriers via any functional groups including amino, carboxyl, hydroxyl and sulfhydryl groups. The immobilization can be established advantageously using compounds (I) containing a biotin moiety which easily binds to an avidin moiety of a resin as the solid phase carrier. In this case, since the molecular weight of the LDL as the ligand is large, a suitable distance between the carrier and peptide is required. This can be accomplished by adjusting the number of bAla of the formula (I), which serves as a spacer.

Examples of solid phase carrier usable in the present invention include those generally used in the pharmaceutical fields such as agarose, acrylic beads, sepharose, dyna beads, latex, cellulose and the like. Among them, a resin bound to avidin, e.g. streptoavidin dyna beads M-280 (manufactured by Dynal Co.) is preferred.

The immobilized peptide of the present invention can be provided in the form of a kit in combination with a suitable device used in the medical fields. For example, it can be charged into a column to obtain a kit to be used as a hemocatharsis apparatus for clarifying circulating blood. Such an apparatus also falls within the scope of the present invention.

The immobilization of the peptide derivatives of the present invention to a solid phase carrier can be conducted in a conventional manner known to persons skilled in the art, for example, by mixing a compound of the formula (III) with Cys-$R^1$ in a buffer of an appropriate pH of about 7.5.

Although the compounds (I) of the present invention can be prepared according to any methods known in the art, they are preferably obtained by the following method. However, the present invention is never limited to the compounds (I) obtained by the following method but includes any compounds prepared by other known methods.

Thus, the compounds of the present invention can be prepared by reacting a compound represented by the formula (II):

Cys-$R^1$ wherein $R^1$ is as defined above with a compound represented by the formula (III).

The present invention provides a process for synthesizing a part of a collagen-like structure of a scavenger receptor, which serves as a modified LDL binding site, while remaining all or a part of 4 lysines associated with binding, or a derivative thereof. As is apparent from the formula (I) above, the compound of the present invention has a structure wherein 3 peptides are bound at their amino-termini in a similar manner to that of a natural collagen-like structure wherein amino-termini are considered to be bound.

According to the method of the present invention, this specific structure is constructed by synthesizing and purifying a single peptide Cys-$R^1$ (II), reacting the peptide (II) with a tri-branched peptide (III), and allowing the respective amino-terminal region of the product to bind together into a triple-stranded form. The peptide (II) of high purity is synthesized conventionally by means of a commercially available automatic peptide synthesizer, which peptide (II) in turn gives the objective triple-stranded peptide (I) with high purity in high yield.

The starting compound (II) is synthesized using an automatic peptide synthesizer, Model 430A, manufactured by Applied Biosystems Co.

The another starting compound, i.e., the branched peptide (III), is also be synthesized by combining any conventional methods used for peptide synthesis and organic synthesis. The coupling reaction between compound (II) and compound (III) is conducted by reacting them in an aqueous solution of 3M guanidine hydrochloride and 0.1M sodium bicarbonate for 6 to 15 hours. The reaction product is purified by subjecting to HPLC, etc.

Figure 4:
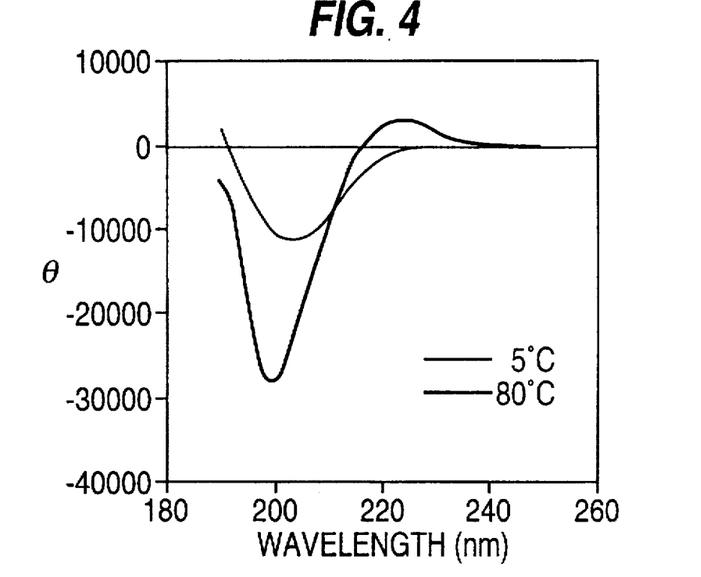
FIG. 4 shows a CD spectrum of a triple-stranded peptide. The CD spectrum was measured using JASCO J-720.

When the resulting compound (I) was subjected to the determination of the binding activity to acetylated LDL labelled by $^{125}$I, the compound proved to have a specific binding activity to acetylated LDL. The measurement of CD spectrum of the compound (I) revealed that it form a collagen-like structure and that the midpoint of heat denaturation is about 30° C. (see, FIGS. 4 and 5).

When using the peptide derivatives of the present invention in clinical treatment, a therapeutically effective amount of a compound (I) can be administered to a patient who requires reduction of blood concentration of modified LDL. The compound (I) can be administered through oral or parenteral route, preferably parenteral route. For such a purpose, the compound of the present invention may be mixed with any of conventional pharmaceutically acceptable carriers, diluents or vehicles and formulated into an appropriate dosage form such as capsules, tablets, powders, granules or the like. In case of parenteral administration, they may be formulated into, for example, solutions or suspensions suitable for subcutaneous injection, intravenous injection, intraperitoneal injection, intramuscular injection or the like.

Alternatively, peptides derivatives (I) are immobilized on suitable solid phase carriers, which can be brought into contact with circulating blood of a patient to be treated at a flow rate of 50 to 70 ml/minute.

The novel peptide derivatives (I) of the present invention may have affinity for the modified LDL in blood and can bind selectively to the same in competition with its natural receptors on macrophages, thereby inhibiting the incorporation of modified LDL into macrophages and/or decreasing the concentration of modified LDL in blood. As a result, the peptide derivatives (I) of the present invention are useful for preventing or treating various circulatory diseases associated with modified LDL, particularly arterial sclerosis. Further, the compounds (I) immobilized on solid phase carriers such as resin, etc. can be used to fix modified LDL in blood onto the solid phase carriers in order to remove the substance or determine the blood level thereof. Thus, the immobilized compound (I) can provide a means of diagnosing, inhibiting or treating arterial sclerosis.

Further, the immobilized peptides (I) of the present invention can be used to detect a peptide capable of binding to the peptide (I) in a mixture of peptides of various amino acid sequences. Accordingly, the present invention can provide a means of screening a peptide capable of binding strongly to a scavenger receptor of a macrophage in competition with modified LDL, thereby contributing to the development of drugs for inhibiting the incorporation of modified LDL into macrophages.

The following Examples further illustrate the present invention in detail but are not to be construed as limiting the scope thereof.

EXAMPLE 1

(1) Synthesis of peptide 4 (SEQ ID NO: 2)

Figure 1:
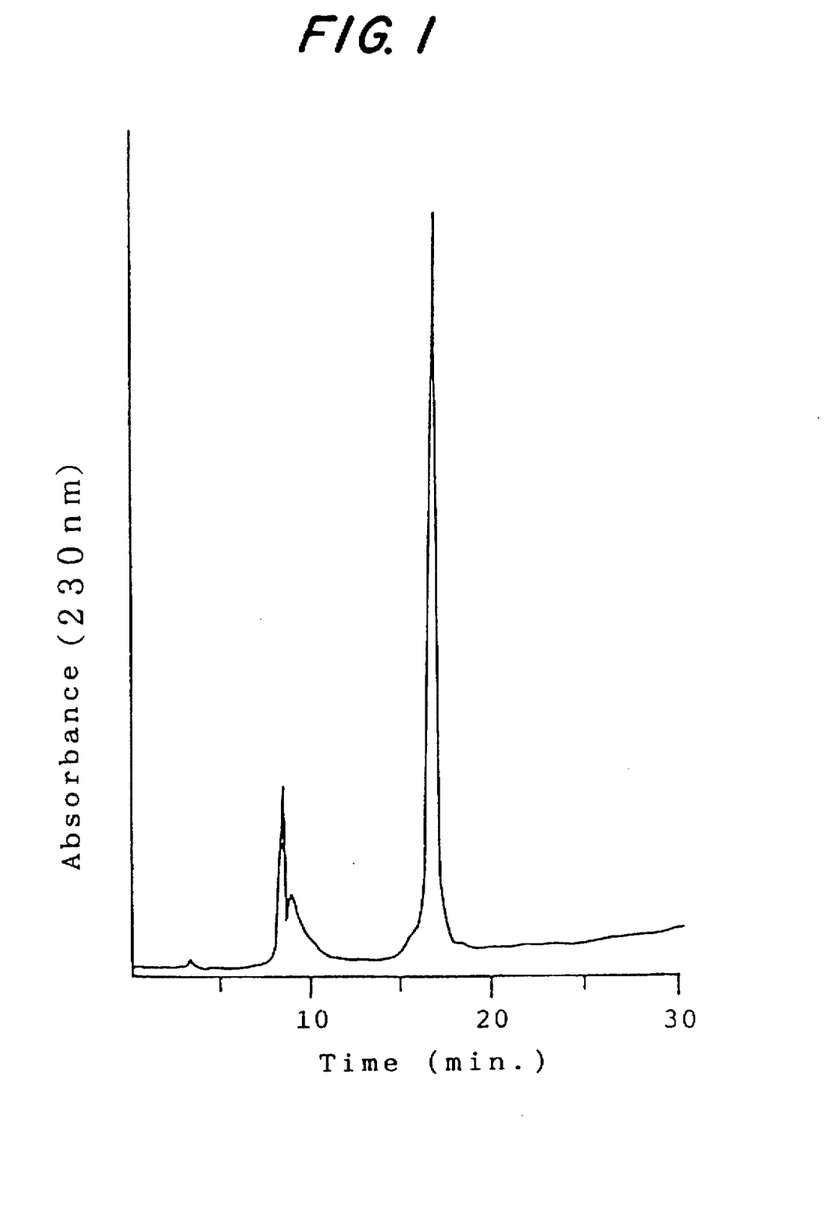
FIG. 1 shows an elution pattern of a single-stranded peptide on high performance liquid chromatography (HPLC). HPLC was conducted by eluting with acetonitrile in 0.1% trifluoroacetic acid at a concentration gradient (10 to 30%) for 30 minutes (flow rate; 1 ml/minute), using TOSOH TSK-GEL ODS120 as a column. The identification of the peptide was conducted by a peptide sequence analysis, amino acid analysis and mass spectrometric analysis.

The peptide 4 was synthesized according to Fmoc method using an automatic peptide synthesizer, Model 430A, manufactured by Applied Biosystems in accordance with the manufacture's instructions. The synthesis was carried out using Rink resins (0.2 mmole, manufactured by Nova Biochem Co.) and a protected amino acid (1 mmole). When the synthesis completed, a resin to which the peptide was bound was removed from the synthesizer. The resin (100 mg) to which the peptide was bound was reacted with ethanedithiol (0.0125 ml, manufactured by Wako Junyaku Co., Ltd.), anisole (0.0375 ml, manufactured by Wako Junyaku Co., Ltd.) and trifluoroacetic acid (0.95 ml, manufactured by Wako Junyaku Co., Ltd.) at room temperature (approximately 25° C.) for 1.5 hours. The reaction solution was poured to cold ether (10 ml) to precipitate a peptide. The precipitated peptide was washed three times with ether (10 ml), dried, dissolved in aqueous acetic acid (5 ml), and subjected to HPLC for purification and lyophilized. An elution pattern of liquid chromatography after purification is shown in FIG. 1. The HPLC was conducted by eluting with acetonitrile in 0.1% trifluoroacetic acid at a concentration gradient of 10 to 30% for 30 minutes, using TOSOH TSK-GEL ODS120 as a column. A flow rate is 1 ml/minute. The compound was identified through the peptide sequencing analysis using Applied Biosystems Model 477A, amino acid analysis using Beckman Mode 6300, and mass spectrometric analysis using ion spray mass SCIEX APII. Results are shown below.

Amino acid analysis (theoretical value is shown in parenthesis):

Cys, 0.3 (1); Gly, 14 (14); Pro, 7.5 (8); 4Hyp, 6.6 (7); Lys, 5.3 (5); Thr, 0.9 (1); Leu, 0.9 (1); Asn/p, 0.8 (1); Gln/u, 2.4 (3).

Ion mass spectrum:

Found value, 3842.7±0.3; and theoretical value for $C_{165}H_{262}O_{54}N_{50}S$, 3842.3.

(2) Synthesis of branched peptide 11

5) Synthesis of compound 10

The compound 9 was subjected to an automatic peptide synthesizer to synthesize the compound 10 according to the above reaction scheme.

7) Synthesis and purification of compound 11

Figure 2:
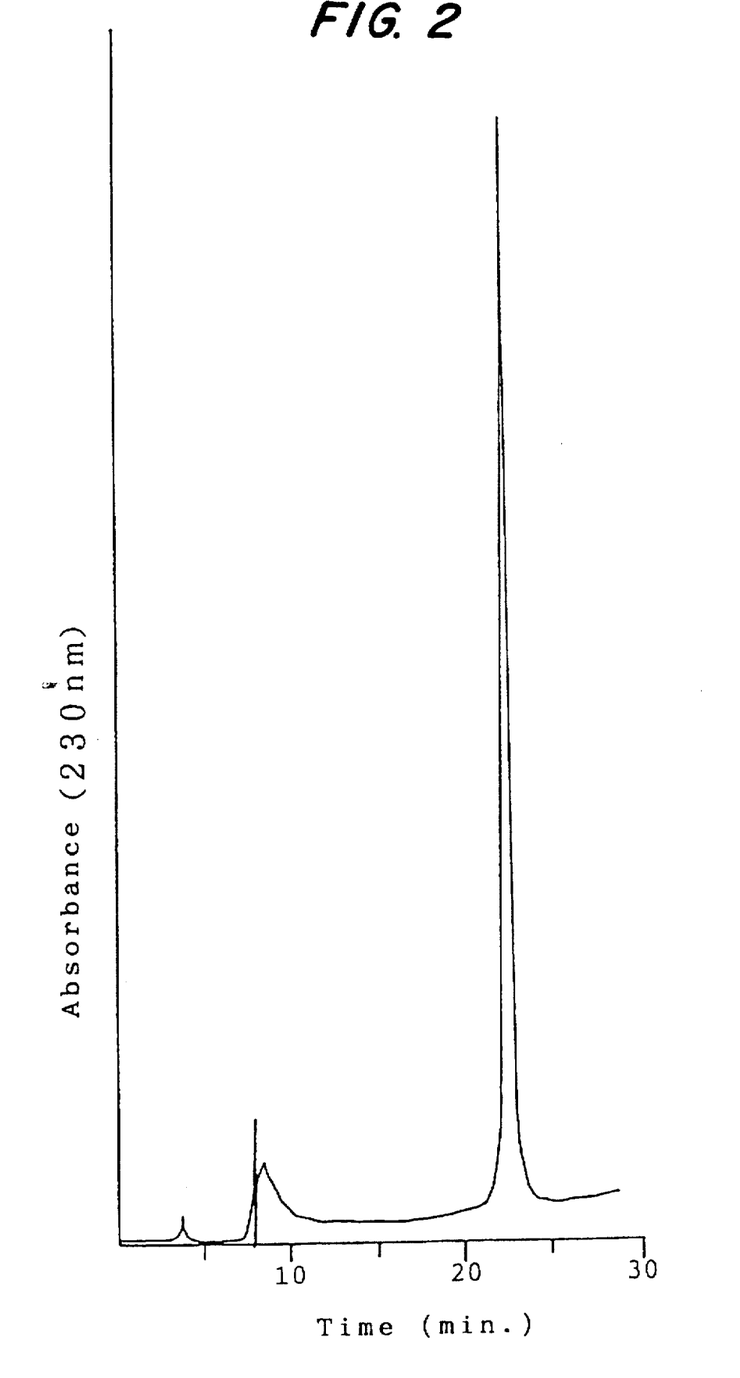
FIG. 2 shows an elution pattern of a biotinated-branched peptide on HPLC in a similar manner to that mentioned in FIG. 1 above.

The resultant peptide-attached resin 10 (100 mg) was reacted with m-cresol (0.1 ml, manufactured by Wako Junyaku Co., Ltd.), trifluoroacetic acid (0.9 ml, manufactured by Wako Junyaku Co., Ltd.) and trifluoromethanesulfonic acid (0.1 ml, manufactured by Applied Biosystems Co.) for 1.5 hours. The reaction solution was ice-cooled, partitioned between water (2 ml) and ether (2 ml) to collect the aqueous phase. The aqueous solution was washed three times with ether (2 ml), purified with HPLC and lyophilized to give the compound 11. An elution pattern of liquid DCC: Dicyclohexylcarbodiimide
HOBt: 4-Hydroxybenzotriazole
BrZ: Bromobenzyloxycarbonyl 1) Synthesis of compound 6

A peptide-attached resin was synthesized by a method shown in the above reaction scheme, using 4-methylbenzhydrylamine resin 5 (manufactured by Peptide Laboratory). The synthesis was conducted by Fmoc method using an automatic peptide synthesizer, Model 430A, manufactured by Applied Biosystems Co in accordance with the manufacture's instructions. The procedures below were conducted manually after removing resin from the synthesizer.

2) Synthesis of compound 7

The reaction between compound 6 (500 mg) and biotin-N-hydroxysuccinimide ester (0.5 mmole) was conducted in N-methylpyrrolidone (4 ml) as a solvent at room temperature for one hour. The reaction product was deprotected by reacting with 50% trifluoroacetic acid in methylene chloride for 15 minutes to give the compound 7.

3) Synthesis of compound 8

The compound 7 was subjected to an automatic peptide synthesizer to synthesize the compound 8 by Fmoc method.

4) Synthesis of compound 9

The compound 8 was deprotected by reacting with 50% trifluoroacetic acid in methylene chloride as a solvent for 15 minutes to give the compound 9.

chromatography after purification is shown in FIG. 2. The HPLC was conducted by eluting with acetonitrile in 0.1% trifluoroacetic acid at a concentration gradient of 15 to 30% for 30 minutes, using TOSOH TSK-GEL ODS120 as a column. A flow rate is 1 ml/minute. The identification of this compound was conducted by mass spectrometry using FAB Mass JEOL JMX-HX100.

FAB mass spectrum: found value $(M+H)^+$, 1803.61; and theoretical value for $C_{73}H_{117}O_{18}N_{18}SBr_3$, 1802.61.

(3) Synthesis of triple-stranded peptide (I)

Figure 3:
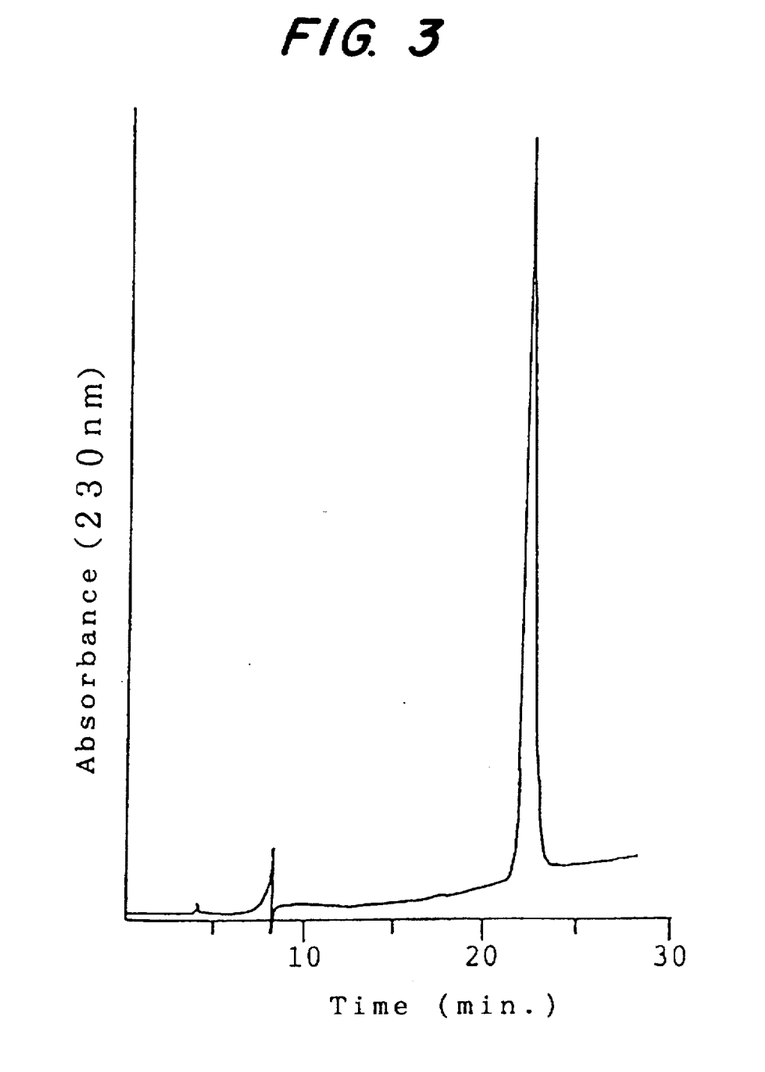
FIG. 3 shows an elution pattern of a collagen model peptide wherein the amino-termini of 3 peptides are bound. HPLC was carried out in a similar manner to that mentioned above.

The peptide 4 (2.37 μmole) prepared in (1) above and branched peptide 11 (0.59 μmole) prepared in (2) above were dissolved in 3M guanidine hydrochloride (2 ml). To the solution was added an aqueous 1M sodium bicarbonate solution (0.2 ml) and reacted for 6 hours. The reaction mixture was acidified with an aqueous 1% trifluoroacetic acid solution, purified with HPLC and lyophilized. An elution pattern of liquid chromatography after purification is shown in FIG. 3. The HPLC was conducted by eluting with acetonitrile in 0.1% trifluoroacetic acid at a concentration gradient of 10 to 30% for 30 minutes, using TOSOH TSK-GEL ODS120 as a column. A flow rate is 1 ml/minute.

The identification of this compound was conducted by amino acid analysis and mass spectrometry. Amino acid analysis (theoretical value is shown in parenthesis):
S-carboxymethylcysteine, 2.9 (3); Gly, 42 (42);
Pro, 22.4 (24); 4Hyp, 19.6 (21); Lys, 18.3 (18);
Thr, 2.8 (3); Leu, 3.0 (3); Asn/p, 2.4 (3);
Gln/u, 7.6 (9); Tyr, 1.2 (1); bAla, 5.5 (6); and
Acp, (2).
Ion mass spectrum:
found value, 13093.1±1.1; theoretical value for $C_{568}H_{900}O_{180}N_{168}S_4$, 13090.7.

(4) CD spectrum of triple-stranded peptide

Figure 5:
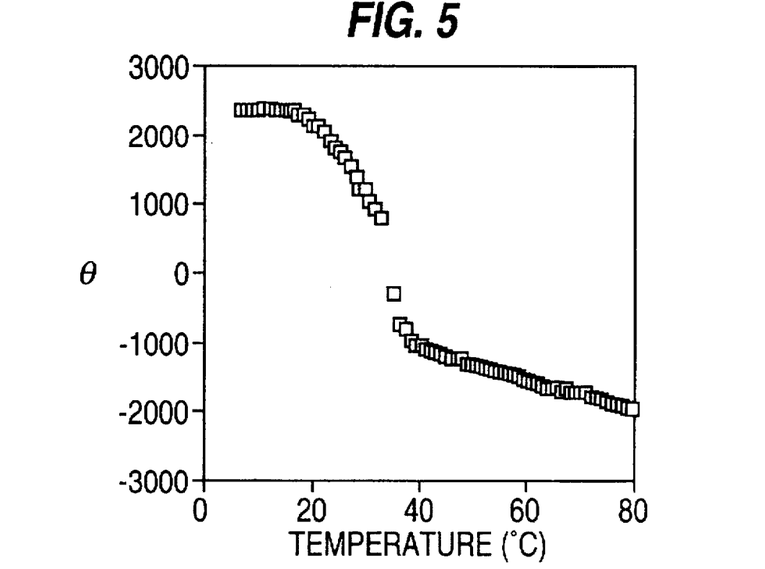
FIG. 5 is a graph showing a state of heat denaturation of a triple-stranded peptide on the basis of the CD spectrum.

The peptide obtained above was dissolved in 5 mM phosphate buffer (pH 7) to obtain a 10 µM solution, which was subjected to the determination of CD spectrum using JASCO J-720. The CD spectrum is characterized by a positive peak at 224 nm and a negative peak at 198 nm (FIG. 4), demonstrating that the peptide takes a collagen structure. The stability against heat was determined by measuring the value at 224 nm, which revealed that the midpoint of the denaturation is about 30° C. (FIG. 5).

100 µl of 10 mM HEPES NaOH (pH 7.4) solution containing 50 mM NaCl and 4 mg/ml of dextran sulfate was added and the mixture was incubated at 4° C. After 1.5 hours, the supernatant was collected and the activity of the free ligand was counted. In another control test, 12 µg of maleic bovine serum albumin was added as a competitive binding inhibitor together with the ligand in the same reaction. Results are shown in FIG. 6.

Figure 6:
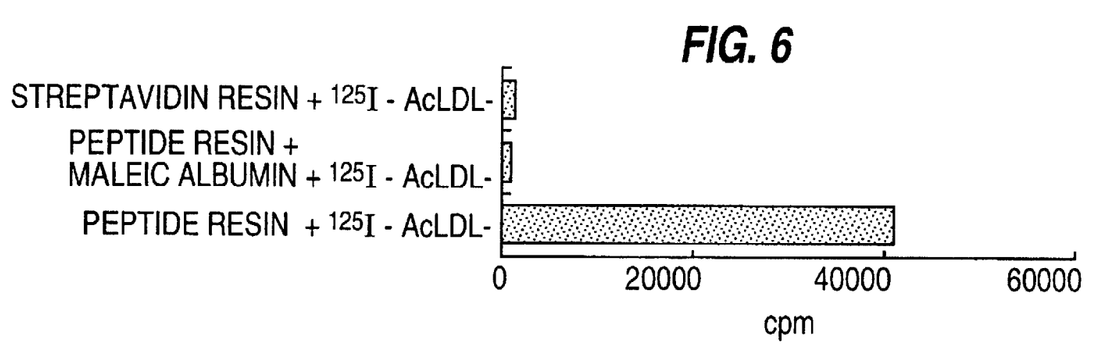
FIG. 6 is a graph showing an amount of AcLDL bound to a peptide resin.

As is clear from FIG. 6, AcLDL was bound to the peptide-immobilized resin of the present invention. On the contrary, in control tests which were carried out using 1) resin to which no peptide immobilized and ligand; and 2) a resin with immobilized peptide, ligand and maleic bovine serum albumin as a competitive inhibitor of AcLDL, no binding effect of AcLDL was observed. These results indicate that AcLDL is successfully bound to the synthetic peptide moiety of the present invention.

EXAMPLE 2

(5) Immobilization of triple-stranded peptide onto solid phase carrier

Streptavidin-dyna beads M-280 (0.2 ml, manufactured by Dynal Co.) were washed twice with 5 mM phosphate buffer (pH 7.5) containing 150 mM NaCl. To the beads was added a peptide solution prepared by dissolving 1 nmole of the peptide obtained above in 0.1 ml of the same phosphate buffer and the mixture was reacted at room temperature for 30 minutes. The resin was washed with the same phosphate buffer. As a result, about 250 pmole of the peptide was bound to the resin.

(6) Determination of binding activity

Either of 32 µl of a solution of streptoavidin-dyna beads M-280, as a control, or 16 µl of a solution of peptide-immobilized dyna beads obtained in (5) above was washed with PBS or DMEM culture medium. The resin was suspended in 80 µl of a DMEM culture medium containing 10% FBS. Then, $^{125}$I-AcLDL (19 µl) as a ligand (1.5 µg, about 0.6 pmole apolipoprotein B-100) was added and the mixture was incubated at 4° C. for 2 hours. After the resin was washed three times with an ice-cooled 50 mM Tris HCl (pH 7.4) solution containing 150 mM NaCl and 2 mg/ml of BSA, According to the reaction scheme above, a compound (I) that is not bound to biotin was synthesized substantially in accordance with the manner that described in Example 1 except for the biotination step (2), 2) in Example 1.

(1) Synthesis of branched peptide 15

1) Synthesis of compound 12

A peptide-attached resin was synthesized by a method shown in the above reaction scheme, using 4-methylbenzhydrylamine resin 5 (manufactured by Peptide Laboratory). The reaction was conducted by Fmoc method using an automatic peptide synthesizer, Model 430A, manufactured by Applied Biosystems Co. according to the manufacture's instructions.

2) Synthesis of compound 13

The compound 12 was removed from the synthesizer and deprotected by reacting with 50% trifluoroacetic acid in methylene chloride for 15 minutes to give a compound 13.

3) Synthesis of compound 14

The compound 13 was re-charged in the automatic peptide synthesizer to synthesize a compound 14 according to the reaction scheme above.

4) Synthesis and purification of compound 15

Figure 7:
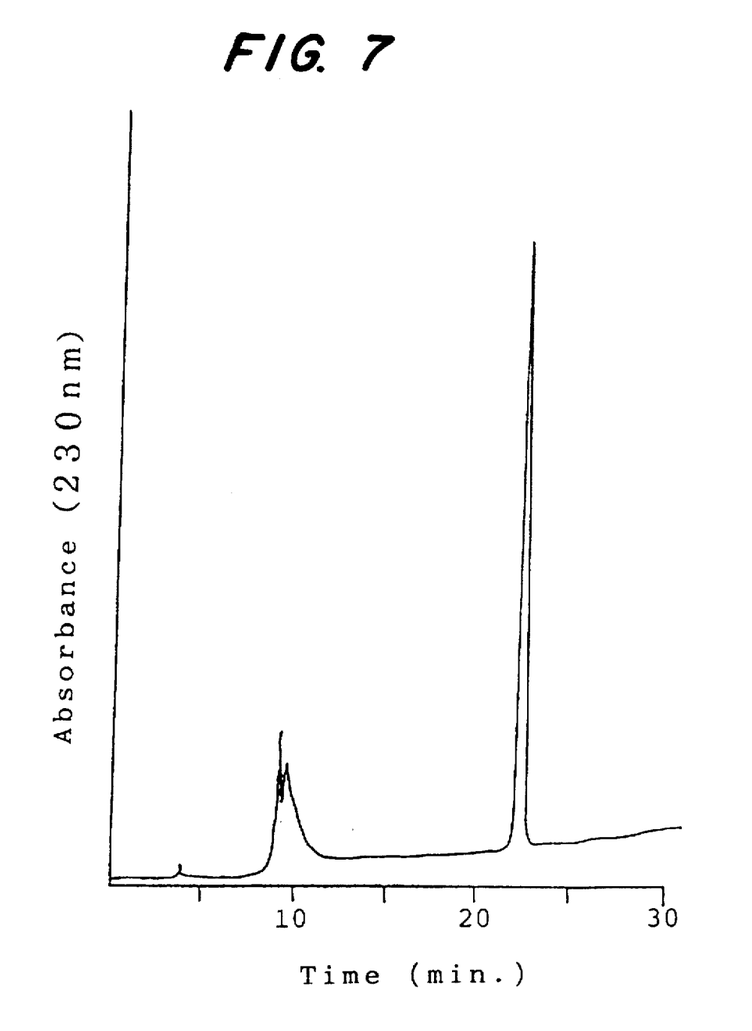
FIG. 7 shows an elution pattern of a non-biotinated-branched peptide.

The peptide-attached resin 14 (100 mg) was treated substantially in accordance with the manner that described in (2) 7) of Example 1 to prepare a compound 15. An elution pattern of liquid chromatography after purification is shown in FIG. 7. The elution was conducted by a concentration gradient of acetonitrile in 0.1% trifluoroacetic acid (10 to 30%) for 30 minutes. FAB mass spectrum: found value $(M+H)^+$, 1280.21; theoretical value for $C_{47}H_{72}O_{14}N_{13}Br_3$, 1279.29.

(2) Synthesis of triple-stranded peptide (I)

Figure 8:
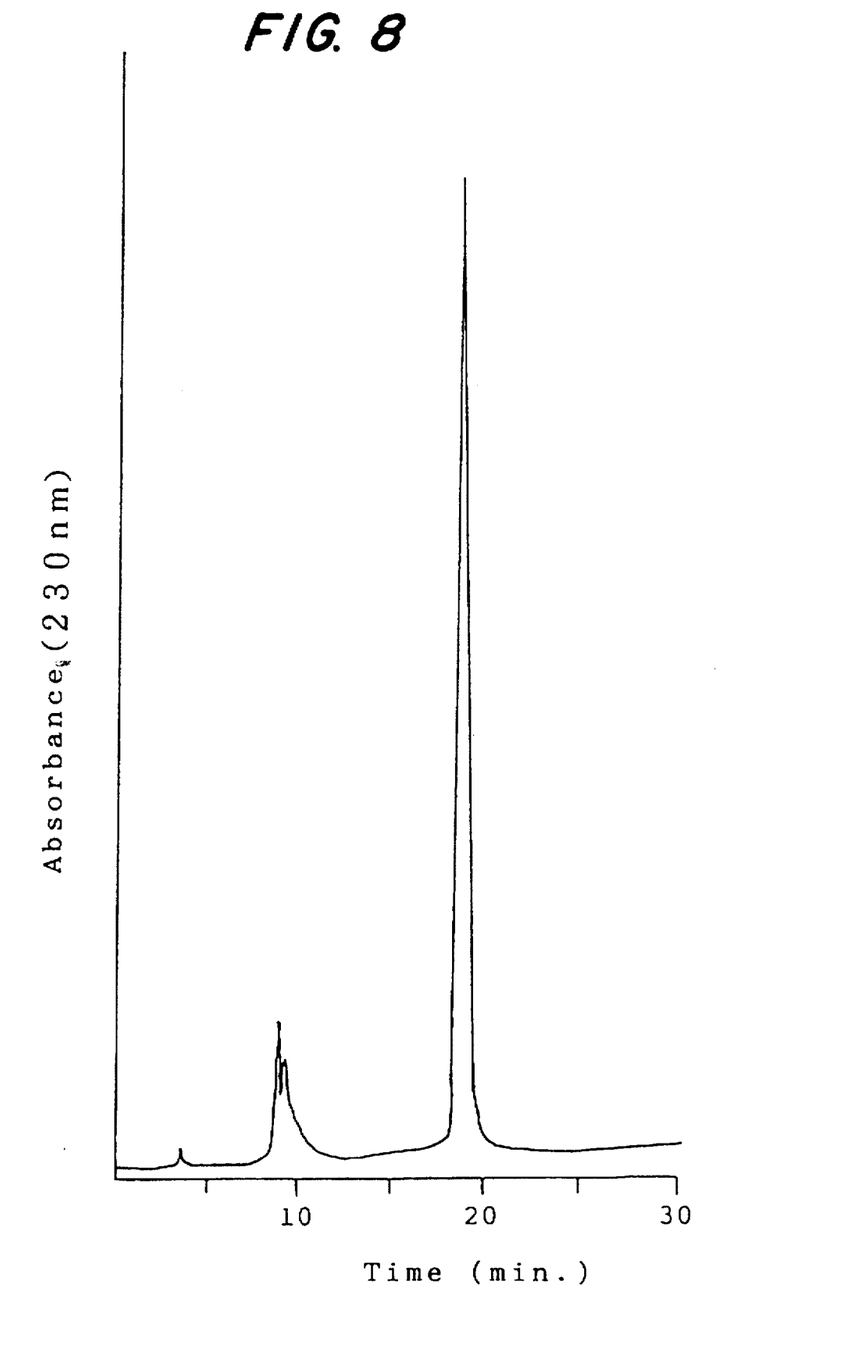
FIG. 8 shows an elution pattern of a non-biotinated collagen model peptide wherein the amino-termini of 3 peptides are bound.

A triple-stranded peptide (I) was prepared by reacting the peptide 4 (2.0 μmole) prepared in Example 1, (1) and the branched peptide 15 (0.5 μmole) prepared in Example 2, (1) substantial in accordance with the manner that described in Example 1, (3). An elution pattern of HPLC after purification is shown in FIG. 8. The elution was conducted by a concentration gradient of acetonitrile in 0.1% trifluoroacetic acid (10 to 30%) for 30 minutes.

Ion mass spectrum:
found value, 12570.0±0.4; and theoretical value for $C_{542}H_{855}O_{176}N_{163}S_3$, 12566.9.

---

What is claimed is:

1. A compound represented by the formula (I):

(I)

wherein bAla is β-alanine;

$R^1$ is a group selected independently from peptide residues represented by the formula:

wherein 4Hyp is 4-hydroxyproline,
$R^2$ is a peptide residue having 9 to 72 amino acids,
$R^3$ is an optionally modified glycine residue, and
q is an integer selected independently from 1 to 10;
n is an integer of 0 to 4;
R is a peptide residue having 0 to 5 amino acids or a group represented by the formula:

wherein Acp is 6-aminocaproic acid; and
R' is a tyrosine compound usable in a quantitative determination of the compound of the formula I.

2. The compound according to claim 1, wherein n is 1 or 2, $R^2$ is a peptide residue which comprises 9 to 72 amino acids containing at least 4 lysine residues and q is 3 or 4.

3. A pharmaceutical composition comprising the compound (I) as claimed in claim 1 or 2 together with a pharmaceutically acceptable carrier, diluent or vehicle.

4. An immobilized peptide wherein the compound (I) as claimed in claim 1 is immobilized on a solid phase carrier.

5. The immobilized peptide according to claim 4, wherein the solid phase carrier is selected from agarose, acrylic beads, sepharose, dyna beads, latex and cellulose.

6. A method for producing the compound (I) as claimed in claim 1, which comprises reacting a compound represented by the formula (II):

wherein $R^1$ is as defined above with a compound represented by the formula (III):

(III)

wherein X is a halogen atom, and R, R', bAla and n are as defined above.

7. A method for inhibiting the incorporation of a modified low density lipoprotein into macrophages, which comprises the step of administering to a patient in need of such treatment a therapeutically effective amount of the pharmaceutical composition according to claim 3.

8. A method for inhibiting or treating arterial sclerosis, which comprises the step of administering to a patient in need of such treatment a therapeutically effective amount of the pharmaceutical composition according to claim 3.

9. A method for recovering or removing a modified low density lipoprotein from blood, which comprises the step of contacting the blood with the immobilized peptide according to claim 4 under conditions wherein the modified low density lipoprotein binds to the immobilized peptide.

10. The compound as claimed in claim 1, wherein R' is an optionally modified tyrosine residue or an optionally modified tryptophan residue.

* * * * *